(12) United States Patent
Kimata et al.

(10) Patent No.: US 7,396,818 B2
(45) Date of Patent: Jul. 8, 2008

(54) SULFOTRANSFERASE INHIBITOR

(75) Inventors: Koji Kimata, Nagoya (JP); Hiroko Habuchi, Nagoya (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 162 days.

(21) Appl. No.: 10/557,652

(22) PCT Filed: May 19, 2004

(86) PCT No.: PCT/JP2004/006750

§ 371 (c)(1),
(2), (4) Date: Nov. 21, 2005

(87) PCT Pub. No.: WO2004/100961

PCT Pub. Date: Nov. 25, 2004

(65) Prior Publication Data

US 2007/0066564 A1    Mar. 22, 2007

(30) Foreign Application Priority Data

May 19, 2003    (JP)    ............................. 2003-140867

(51) Int. Cl.
*A01N 43/04* (2006.01)
*A61K 31/70* (2006.01)
*C07H 15/00* (2006.01)
*C07H 15/06* (2006.01)

(52) U.S. Cl. ........................................ 514/25; 536/18.2
(58) Field of Classification Search .................. None
See application file for complete search history.

(56) References Cited

U.S. PATENT DOCUMENTS

| 5,075,433 | A | 12/1991 | Weis |
| 5,817,487 | A | 10/1998 | Kobayashi et al. |
| 5,834,282 | A | 11/1998 | Habuchi et al. |
| 2004/0053253 | A1 | 3/2004 | Habuchi et al. |

FOREIGN PATENT DOCUMENTS

| EP | 0 756 004 | 1/1997 |
| JP | 11-069983 | 3/1999 |
| JP | 2000-060566 | 2/2000 |
| JP | 2001-057882 | 3/2001 |
| WO | WO 99/50385 | 10/1999 |

OTHER PUBLICATIONS

Rath et al. DDT vol. 9, No. 23, Dec. 2004, pp. 1003-1011.*
Wessel et al. Carbohydrate Research 1995, 274, 1-9.*
International Search Report dated Jul. 12, 2004.
Aikawa, et al. "Molecular Cloning and Expression of a Third Member of the Heparan Sulfate/Heparin GlcNAc N-Deacetylase1," *The Journal of Biological Chemistry*, vol. 274, No. 5, pp. 2690-2695, Jan. 29, 1999.

Hashimoto, et al. "Molecular Cloning and Expression of Rat Liver N-Heparan," *The Journal of Biological Chemistry*, vol. 267, No. 22, pp. 15744-16750, Aug. 5, 1992.
Hortin, et al. "Inhibitors of the Sulfation of Proteins, Glycoproteins, and Proteoglycans," *Biochemical and Biophysical Research Communications*, vol. 150, No. 1, pp. 342-348, Jan. 15, 1988.
Ishihara, Masayuki. "Structural Requirements in Heparin for Binding and Activation of FGF-1 and FGF-4 are Different from that for FGF-2," *Glycobiology*, vol. 4, No. 6, pp. 817-824, 1994.
Ishihara, et al. "Structural Features in Heparin Which Modulate Specific Biological Activities Mediated by Basic Fibroblast Growth Factor," *Glycobiology*, vol. 4, No. 4, pp. 451-458, 1994.
Orellana, et al. "Molecular Cloning and Expression of a Glycosaminoglycan N-Acetylglucosaminyl N-Deacetylase1N-Sulfotransferase from a Heparin-Producing Cell Line," *The Journal of Biological Chemistry*, vol. 269, No. 3, pp. 2270-2276, Jan. 21, 1994.
Sugumaran, et al. "Effects of Brefeldin A on the Localization of Chondroitin Sulfate-Synthesizing Enzymes," *The Journal of Biological Chemistry*, vol. 267, No. 13, pp. 8802-8806, May 5, 1992.
Abstracts of the XV International Symposium on Glycoconjugates 1999; 16:S40.
Hashimoto, et al. "Molecular Cloning and Expression of Rat Liver N-Heparan," *The Journal of Biological Chemistry*, vol. 267, No. 22, pp. 15744-15750, Aug. 5, 1992.

(Continued)

*Primary Examiner*—Shaojia Anna Jiang
*Assistant Examiner*—Layla Bland
(74) *Attorney, Agent, or Firm*—Knobbe, Martens, Olson & Bear, LLP (57) ABSTRACT

The hexuronic acid derivative represented by the following formula 1 or a salt thereof is used as an active ingredient of a heparin/heparan sulfate sulfotransferase inhibitor.

[Chemical formula 1]

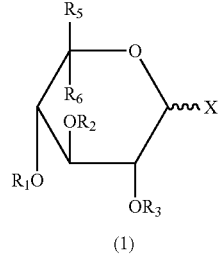

(1)

In the formula, each of $R_1$, $R_2$, and $R_3$ independently represent(s) $SO_3^-$ or H which may have a substituent, provided that at least one thereof represents $SO_3^-$; X represents $OR_4$, $SR_4$, $N(R_4)_2$, or $C(R_4)_3$, $R_4$ independently represents H, alkyl, alkenyl, alkynyl, acyl, aryl, or aralkyl group; one of $R_5$ and $R_6$ represents COOH while the other represents H; and the wavy line represents α-glycosidic bond or β-glycosidic bond.

4 Claims, 5 Drawing Sheets

OTHER PUBLICATIONS

Bielicki, et al. "Human Liver Iduronate-2-Sulphatase," *Journal of Biochemistry*, vol. 271, No. 1, pp. 75-86, 1990.

Supplementary European Search Report dated Apr. 16, 2007.

Ii, et al. "Characterization of Positional and Anomeric Isomers of Methyl 2-O- and 3-O-Sulfo-D-Glucopyranosiduronic Acids and Methyl 2-O- and 3-O-Sulfo-D-Glucopyranosides by Secondary Ion Mass Spectrometry," *Organic Mass Spectrometry*, vol. 28, pp. 789-794, 1993.

* cited by examiner

SULFOTRANSFERASE INHIBITOR

This application is the U.S. National Phase under 35 U.S.C. § 371 of International Application PCT/JP2004/006750, filed May 19, 2004, which was published in a language other than English, which claims priority of Japanese Patent Application No. 2003-140867, filed May 19, 2003.

TECHNICAL FIELD

The present invention relates to an inhibitor capable of specifically inhibiting activity of a particular heparin/heparan sulfate sulfotransferase, more specifically to an inhibitor which inhibits activity of sulfotransferase to transfer a sulfate group to a hydroxyl group at 6-position of a glucosamine residue in a basic skeleton of heparin/heparan sulfate that is a kind of glycosaminoglycans (hereinafter also referred to as "heparin skeleton") or activity of heparin/heparan sulfate sulfotransferase to transfer a sulfate group to a hydroxyl group at 2-position of a hexuronic acid residue in a basic skeleton of heparin/heparin sulfate.

BACKGROUND OF THE INVENTION

Heparin/heparan sulfate is one of the glycosaminoglycans having sulfate groups, and has a basic skeleton composed of serial disaccharides linked each other via β1-4 glycosidic bonds (in the present specification, also referred to as "heparin skeleton"). The disaccharides are formed by binding hexuronic acid (i.e. D-glucuronic acid or L-iduronic acid whose hydroxyl group(s) at 2- and/or 3-position may be sulfated) and glucosamine (i.e. N-acetylglucosamine whose acetylamino group(s) may be substituted by a sulfamino group, and/or hydroxyl group(s) at 6-position may be sulfated) via β1-4 glycosidic bonds when the hexuronic acids are D-glucuronic acids, and via α1-4 glycosidic bonds when the hexuronic acids are L-iduronic acids.

In addition to such glycosaminoglycans as heparin/heparan sulfate, many of proteoglycans, glycoproteins, and glycolipids have sulfate groups, and many sulfotransferases are involved in the biosynthesis thereof. For example, as an enzyme which transfers a sulfate group to a heparin skeleton, JP09-28374A discloses an enzyme (HS2ST) that has activity to transfer a sulfate group to a hydroxyl group at 2-position of hexuronic acid in a heparin skeleton. Moreover, JP08-33483A discloses an enzyme (HS6ST) that has activity to transfer a sulfate group to a hydroxyl group at 6-position of a glucosamine residue in a heparin skeleton. Furthermore, JP2000-60566A and WO 02/000889 disclose related enzymes (HS6ST2, HS6ST3) and a variant (HS6STv) of the HS6ST disclosed in JP08-33483A. Furthermore, J. Biol. Chem., 267 (1992), pp. 15744-15750; J. Biol. Chem., 269 (1994), pp. 2270-2276; J. Biol. Chem., 274 (1999), pp. 22458-22465; and Glycoconj. J., 16 (1999), S40 disclose enzymes (NDST-1, NDST-2, NDST-3, NDST4) each having activity to deacetylate an acetylamino group of a glucosamine residue in a heparin skeleton and then to sulfate it.

Meanwhile, it is known that heparin or heparan sulfate has high affinity to growth factors, and it is known that the affinity to various cytokines or growth factors varies depending on a position and degree of sulfation of heparin or heparan sulfate (Glycobiology, 4(1994), 451 or Glycobiology, 4(1994), 817).

Therefore, it is highly likely that an inhibitor, which inhibits activity of such heparin/heparan sulfate sulfotransferase deeply involved in biosynthesis of heparin, heparan sulfate, or the like, can be applied to, for example, an anti-cancer drug using its anti-angiogenic effect, a cancer metastasis inhibitor using its effect to inhibit adhesion to ECM, an anti-allergic drug or an anti-rheumatic drug using its effect to inhibit heparin synthesis in mast cells in connective tissues.

Known examples of such an inhibitor for a sulfotransferase include chlorate described in Biochem. Biophys. Res. Commun., 150 (1988), pp. 342-348, brefeldin A described in J. Biol. Chem., 267 (1992), pp. 8802-8806, etc. The former inhibits a sulfotransferase by exerting a nonspecific competitive inhibitory effect on the enzyme, while the latter inhibits the enzyme by destroying Golgi apparatus where a sugar chain is synthesized. Therefore, those conventional inhibitors may cause side effects, because specificity of their inhibitory effect on biosynthesis of heparin/heparan sulfate is low and they strongly inhibit not only biosynthesis of heparin/heparan sulfate but also biosynthesis of other glycosaminoglycans, proteoglycans, or glycoproteins, so that it is highly unlikely that they can be used as therapeutic agents for diseases.

DISCLOSURE OF THE INVENTION

Accordingly, there has been a need for a novel sulfotransferase inhibitor using a compound that has a highly specific inhibitory activity to a particular heparin/heparan sulfate sulfotransferase and can be safely administered to a living body.

The inventors of the present invention have made extensive studies to solve the above-described problems. As a result, they found that a "hexuronic acid derivative" formed by binding, via a glycosidic bond, a hydrogen atom or aglycon molecule to an anomeric carbon (carbon at 1-position) of "hexuronic acid in which a hydroxyl group at 2-, 3-, and/or 4-position is sulfated" has an excellent heparin/heparan sulfate sulfotransferase inhibitory activity, thereby they completed the present invention.

That is, the present invention is as follows.

(1) A heparin/heparan sulfate sulfotransferase inhibitor, which comprises a hexuronic acid derivative represented by the following formula 1 or a salt thereof, in an effective amount for inhibition of the enzyme.

[Chemical formula 1]

(1)

In the formula, each of $R_1$, $R_2$, and $R_3$ independently represent(s) $SO_3^-$ or H which may have a substituent, provided that at least one thereof represents $SO_3^-$; X represents $OR_4$, $SR_4$, $N(R_4)_2$, or $C(R_4)_3$, $R_4$ independently represents H, alkyl, alkenyl, alkynyl, acyl, aryl, or aralkyl group; one of $R_5$ and $R_6$ represents COOH while the other represents H; and the wavy line represents α-glycosidic bond or β-glycosidic bond.

(2) The heparin/heparan sulfate sulfotransferase inhibitor according to (1), wherein, in the formula 1, $R_1$ represents H; one of $R_2$ and $R_3$ represents $SO_3^-$ while the other represents H, or both of them represent $SO_3^-$; X represents $OR_4$, $R_4$ represents an alkyl group having 6 or less carbon atoms; $R_5$ represents COOH; and $R_4$ represents H.

(3) The heparin/heparan sulfate sulfotransferase inhibitor according to (1) or (2), which inhibits activity of heparin/ heparan sulfate sulfotransferase to transfer a sulfate group to a hydroxyl group at 6-position of a glucosamine residue in a heparin skeleton.

(4) The heparin/heparan sulfate sulfotransferase inhibitor according to (1) or (2), which inhibits activity of heparin/heparan sulfate sulfotransferase to transfer a sulfate group to a hydroxyl group at 2-position of a hexuronic acid residue in a heparin skeleton.

(5) Use of a hexuronic acid glycoside derivative represented by the following formula 1 or a salt thereof as a heparin/heparan sulfate sulfotransferase inhibitor.

[Chemical formula 2]

(1)

In the formula, each of $R_1$, $R_2$, and $R_3$ independently represent(s) $SO_3^-$ or H which may have a substituent, provided that at least one thereof represents $SO_3^-$; X represents $OR_4$, $SR_4$, $N(R_4)_2$, or $C(R_4)_3$, $R_4$ independently represents H, alkyl, alkenyl, alkynyl, acyl, aryl, or aralkyl group; one of $R_5$ and $R_6$ represents COOH while the other represents H; and the wavy line represents α-glycosidic bond or β-glycosidic bond.

(6) A pharmaceutical composition which comprises the heparin/heparan sulfate sulfotransferase inhibitor according to any one of (1) to (4) as an active ingredient.

(7) A method of inhibiting a sulfate group-transferring activity of an enzyme having activity to transfer a sulfate group from a sulfate group donor to a sugar chain that has a heparin skeleton and serves as a sulfate group acceptor, comprising using the heparin/heparan sulfate sulfotransferase inhibitor according to any one of (1) to (4).

DESCRIPTION OF THE PREFERRED EMBODIMENTS

Hereinafter, the present invention will be described in detail by way of embodiments thereof.

(1) Inhibitor of the Present Invention

The inhibitor of the present invention is a heparin/heparan sulfate sulfotransferase inhibitor, which comprises a hexuronic acid derivative represented by the following formula 1 or a salt thereof, in an effective amount for enzyme inhibition.

[Chemical formula 3]

(1)

sulfated hexuronic acid residue moiety

In the formula, each of $R_1$, $R_2$, and $R_3$ independently represent(s) $SO_3^-$ or H, provided that at least one thereof represents $SO_3^-$; X represents $OR_4$, $SR_4$, $N(R_4)_2$, or $C(R_4)_3$, in which $R_4$ independently represents H, alkyl, alkenyl, alkynyl, acyl, aryl, or aralkyl group; one of $R_5$ and $R_6$ represents COOH while the other represents H; and the wavy line represents α-glycosidic bond or β-glycosidic bond.

In the sulfated hexuronic acid residue (the moiety referred to as "sulfated hexuronic acid residue moiety" in the above-described formula) that forms a hexuronic acid derivative represented by the formula 1, which serves as an active ingredient of the inhibitor of the present invention, either $R_5$ may be a carboxyl group (COOH) (in this case, $R_6$ is a hydrogen atom (H), and the "sulfated hexuronic acid residue" is a "sulfated glucuronic acid residue") or $R_6$ may be a carboxyl group (COOH) (in this case, $R_5$ is a hydrogen atom (H), and the "sulfated hexuronic acid residue" is a "sulfated iduronic acid residue"). In the "sulfated hexuronic acid residue", $R_5$ is preferably a carboxyl group (that is, the sulfated hexuronic acid residue is preferably a sulfated glucuronic acid residue).

Meanwhile, the hydrogen atoms of hydroxyl groups at 2-, 3-, and 4-positions of the sulfated hexuronic acid residue may independently be substituted by a sulfate group, and it is necessary that at least one thereof is substituted by a sulfate group. That is, in the above-described formula, it is necessary that each of $R_1$, $R_2$, and $R_3$ independently represent $SO_3^-$ or H, provided that at least one thereof represents $SO_3^-$. A hexuronic acid derivative, in which any one of $R_1$, $R_2$, and $R_3$ is $SO_3^-$ and the others are H, is preferable. A hexuronic acid derivative, in which one of $R_2$ and $R_3$ is $SO_3^-$, the other is H and $R_1$ is H, is particularly preferable.

In the above-described formula 1, X can be represented $OR_4$, $SR_4$, $N(R_4)_2$, or $C(R_4)_3$. That is, $R_4$ (($R_4$), ($R_4$)$_3$) binds to the sulfated hexuronic acid moiety in the formula 1 via an O-glycosyl bond (glycosidic bond), S-glycosyl bond, N-glycosyl bond (in the case that one of $R_4$ is H, an imino group is formed), or C-glycosyl bond. Of those, the O-glycosyl bond is particularly preferable. In $N(R_4)_2$ and $C(R_4)_3$, two $R_4$ that bind to N and three $R_4$ that bind to C are independent with each other and may have different structures.

The above-described glycosyl bond may be an α-glycosyl bond or a β-glycosyl bond (the bond represented by a wavy line in the formula 1). In particular, the β-glycosyl bond is preferable. Herein, "α" and "β" represent anomers of a glycosyl bond at 1-position of the sugar ring, and when the positional relationship between the bond and COOH that binds to a carbon atom at 5-position ($R_5$ or $R_6$ described above) is trans configuration, the bond is represented as "α", whereas when the positional relationship is cis configuration, the bond is represented as "β".

$R_4$ represents a hydrogen atom (H) or an aglycon that is generally used for modification or protection of a sugar, and the aglycon is more preferable than hydrogen atom. Examples of such an aglycon include alkyl, alkenyl, alkynyl, acyl, aryl, and aralkyl groups. Of those, an alkyl group is preferable.

The above-described alkyl group is preferably a linear or branched alkyl group comprising 20 or less carbon atoms (the number means the number of carbon atoms other than those of substituents). The alkyl group may be modified with other substituent and for example, it may be an alkoxyalkyl group having a skeleton derived from an alkylglycerol or an acyloxyalkyl group having a skeleton derived from an acylglycerol as shown in the formula 2 shown below (in the following formula, l and m independently represent an integer of 0 to 18, and Z independently represents a methylene or carbonyl group).

[Chemical formula 4]

(2)

In particular, the alkyl skeleton moiety other than the above-described substituents such as alkoxy group and acyloxy group in the alkyl group represented by the formula 2 is a linear lower alkyl group having 1 to 6, preferably 1 to 4 carbon atoms. Of those, particularly preferable is a methyl group that is an alkyl group having one carbon atom (each number means the number of carbon atoms other than those of substituents).

In the above-described alkenyl and alkynyl groups, the number of carbon atoms in the above-described alkenyl or alkynyl skeleton moiety other than those of substituents is 2 to 10, preferably 2 to 6, most preferably 2 to 4 (each number means a number of carbon atoms other than those of substituents). In the case of the alkenyl or alkynyl group, the group may have plural double bonds or triple bonds of carbon atoms.

The above-described acyl group may be any group so long as it is generally represented as —CO—R, and the number of carbon atoms other than above-described substituents in the moiety represented as R is 1 to 10, preferably 1 to 6, most preferably 1 to 4. In the above-described formula, R is any group selected from alkyl, alkenyl, and alkynyl groups as described above, and aryl and aralkyl groups described below, all of which may have a substituent. The above-described "number of carbon atoms" means a number of carbon atoms other than those of such substituents.

The above-described aryl group is preferably aromatic hydrocarbon residue having 6 to 22 carbon atoms, and examples thereof include an aromatic hydrocarbon residue such as a phenyl or naphthyl group, and an aromatic residue (such as a tolyl group) that has a structure of those aromatic hydrocarbon residues whereby a hydrogen atom in the aromatic ring is further substituted by a substituent. Of those, phenyl and naphthyl groups each having no substituent are preferable, and a phenyl group is particularly preferable.

The above-described aralkyl group is a residue formed by replacing a hydrogen atom in an alkyl group by one or more aryl groups (Ar), and the number of carbon atoms in the alkyl group moiety other than the aryl groups is preferably 1 to 10, more preferably 1 to 6. The aralkyl group may have a substituent. Examples of the aralkyl group include benzyl, phenethyl, and α-methylbenzyl groups.

Examples of the "substituent" in the above-described hexuronic acid derivative include alkyl, acyl, alkoxyl, hydroxyl (OH) groups, halogen atoms (fluorine atom (F), chlorine atom (Cl), bromine atom (Br), iodine atom (I), etc.), nitro ($NO_2$), sulfate ($SO_3^-$), OXO, carboxyl (COOH), and amino ($NH_2$, NH) groups. Meanwhile, examples of substituents in alkyl, alkenyl, alkynyl, acyl, aryl, and aralkyl groups include a hydroxyl group, halogen atom, nitro, sulfate, oxo, carboxyl, and amino groups.

A six-membered ring that constitutes a sugar exists in a chair conformation or in a boat conformation. The hexuronic acid derivative that serves as an active ingredient of the inhibitor of the present invention may exist in any of the two forms, and preferably exists in a chair conformation from the viewpoint of stability.

Therefore, examples of the most preferable hexuronic acid derivative include substances represented by the following formulae 3 and 4.

[Chemical formula 5]

(3)

-continued

[Chemical formula 6]

(4)

In these formulae, each wavy line means an α-glycoside or β-glycosidic bond that binds to a sulfated hexuronic acid residue moiety. Meanwhile, hydrogen atoms that bind to carbon atoms are omitted in these formulae.

The above-described hexuronic acid derivative may be used as an active ingredient of the inhibitor of the present invention even in the form of a salt with a counter ion. Examples of the counter ion include a cation (a metal ion such as sodium ion, potassium ion and lithium ion, or an onium cation such as triethylamine and pyridine) capable of forming a salt with a carboxyl or sulfate group in the above-described formulae, and an acidic ion (such as hydrochloride ion, sulfate ion, mesylate ion, or p-toluenesulfonate ion) that forms an acid addition salt (such as hydrochloride, sulfate, mesylate and p-toluenesulfonate) with an imino group such as N-glycoside that binds to the carbon atom at 1-position of hexuronic acid or the like. The above-described hexuronic acid derivative may form a salt with alternatively either a metal ion or an acidic ion, or may form a salt (double salt) with both of them. In the case that the inhibitor of the present invention is used as a drug, the salt is particularly preferably a pharmacologically acceptable salt. Examples of a preferable pharmacologically acceptable salt comprising a cation include that of sodium ion or potassium ion, while examples of a preferable pharmacologically acceptable salt as an acid addition salt include that of hydrochloride ion.

For the sake of convenience, the hexuronic acid derivative that is represented by the above-described formula 3 and has an α-glycosidic bond is referred to as "Derivative 1", while the hexuronic acid derivative that is represented by the above-described formula 3 and has a β-glycosidic bond is referred to as "Derivative 2". Meanwhile, the hexuronic acid derivative that is represented by the above-described formula 4 and has an α-glycosidic bond is referred to as "Derivative 3", while the hexuronic acid derivative that is represented by the above-described formula 4 and has a β-glycosidic bond is referred to as "Derivative 4".

Those derivatives (Derivatives 1 to 4) can be prepared according to, for example, the method described in Carbohyd. Res., 198 (1990), pp 133-140.

A heparin/heparan sulfate sulfotransferase inhibitory effect of the hexuronic acid derivative can be confirmed as follows: the derivatives are allowed to coexist with heparin/heparan sulfate sulfotransferase (in particular, sulfotransferases described in JP08-33483A and JP09-28374A) and a substrate of the enzyme (sulfate group donor and sulfate group acceptor), and the enzyme activity of heparin/heparan sulfate sulfotransferase is determined, followed by comparison of the results with those in the absence of the derivatives.

Heparin/heparan sulfate sulfotransferase, the enzyme activity of which is inhibited by the inhibitor of the present invention, is an enzyme having activity to transfer a sulfate group from a sulfate group donor to a sugar chain that has a heparin skeleton such as heparin/heparan sulfate and serves as a sulfate group acceptor. Among those, an enzyme having activity to transfer a sulfate group to a hydroxyl group at 6-position of a glucosamine residue in a heparin skeleton (heparan sulfate 6 sulfotransferase: HS6ST, HS6ST2, HS6ST2v, HS6ST3), an enzyme having activity to transfer a sulfate group to a hydroxyl group at 2-position of a hexuronic acid residue in a heparin skeleton (heparan sulfate 2 sulfotransferase: HS2ST), and an enzyme having activity to transfer a sulfate group to an amino group at 2-position of a glucosamine residue in a heparin skeleton (heparan sulfate N deacetylated sulfotransferase: NDST-1, NDST-2, NDST-3, NDST-4) are preferable. Of those, HS2ST, HS6ST, HS6ST2, HS6ST3, and HS6ST2v are more preferable, HS2ST and HS6ST are particularly preferable, and HS6ST is most preferable.

In the case that an enzyme activity in a reaction system where the inhibitor of the present invention is not added (control) and an enzyme activity in a system where an enzyme is not added (negative control) are defined as 100% and 0, respectively, the activity of the inhibitor of the present invention to inhibit the enzyme activity means the activity to lower the enzyme activity by 5% or more compared with that of the control. In particular, when the inhibitory activity is determined according to a determination method of an inhibitory activity described in Example 1 below, the inhibitor of the present invention inhibits enzyme activity by 5% or more, preferably 10% or more, most preferably 15% or more in the case of a reaction using the inhibitor at a concentration of 2.5 mmol/l.

By utilizing the above-described effect of the inhibitor of the present invention to inhibit heparin/heparan sulfate sulfotransferase, the inhibitor can be used as a reagent for research or as a pharmaceutical composition.

The pharmaceutical composition of the present invention may contain other ingredients as long as it contains an effective amount of the above-described hexuronic acid derivative. For example, the pharmaceutical composition of the present invention may be produced by using the above-described hexuronic acid derivative in combination with a pharmaceutically acceptable carrier. The pharmaceutical carrier is not particularly limited, and examples of the carrier include a filler, binder, disintegrator, lubricant, stabilizer, flavoring agent, diluent, surfactant, and solvent for injection, each of which is generally used for drugs. In the pharmaceutical composition of the present invention, the above-described hexuronic acid derivative may be a pharmaceutically acceptable salt. The pharmaceutically acceptable salt includes both a metal salt (inorganic salt) and organic salt, and examples thereof include: inorganic salts such as hydrochloride, sulfate, phosphate, diphosphate, hydrobromide, and sulfate; and organic salts such as malate, maleate, fumarate, tartrate, succinate, citrate, acetate, lactate, methanesulfonate, p-toluenesulfonate, pamoate, salicylate, and stearate. Meanwhile, each of those salts may be a salt formed with a metal such as sodium, potassium, calcium, magnesium, or aluminum; or a salt formed with an amino acid such as lysine. Moreover, the pharmaceutical composition of the present invention includes a solvate such as a hydrate of the above-described hexuronic acid derivative or a pharmaceutically acceptable salt thereof.

The dosage form of the inhibitor of the present invention is not particularly limited and may be appropriately selected depending on the therapeutic purpose, and specific examples thereof include a tablet, pill, powder, liquid, suspension, emulsion, granule, capsule, syrup, suppository, injection, ointment, patch, ophthalmic solution, and nasal drop.

The pharmaceutical composition of the present invention may suitably be used for treatment or prevention of a disease that is caused by elevation of heparin/heparan sulfate sulfotransferase activity. Examples of the disease include cancer, allergy and rheumatism. The composition may be used as an anti-cancer drug utilizing an anti-angiogenic effect of the inhibitor of the present invention, cancer metastasis inhibitor utilizing its effect to inhibit adhesion to ECM, anti-allergic drug and anti-rheumatic drug utilizing its effect to inhibit heparin synthesis in mast cells in connective tissues, and the like.

The pharmaceutical composition of the present invention may be orally or parenterally administered to mammals including human. The timing of administration is not particularly limited and may appropriately be selected according to a method of treating a target disease. Meanwhile, the administration form is preferably determined depending on a dosage form, and age, sex, other conditions, degree of symptom, etc. of a patient.

The dose of an active ingredient of the pharmaceutical composition of the present invention is appropriately selected depending on a dose regimen, age, sex, degree of a disease, other conditions, etc. of a patient. Usually, the amount of hexuronic acid derivative as an active ingredient may be preferably in the range of 0.01 to 100 mg/kg/day, more preferably 0.1 to 10 mg/kg/day. The active ingredient may be administered in once or several times a day.

EXAMPLES

Hereinafter, the present invention will be described in more detail by way of examples.

All hexuronic acid derivatives used in Examples (Derivatives 1 to 4) were prepared according to the description in Carbohyd. Res., 198 (1990), pp 133-140. Meanwhile, HS2ST and HS6ST used in Examples were prepared according to JP09-28374A and JP08-98684A.

Example 1

Figure 1:
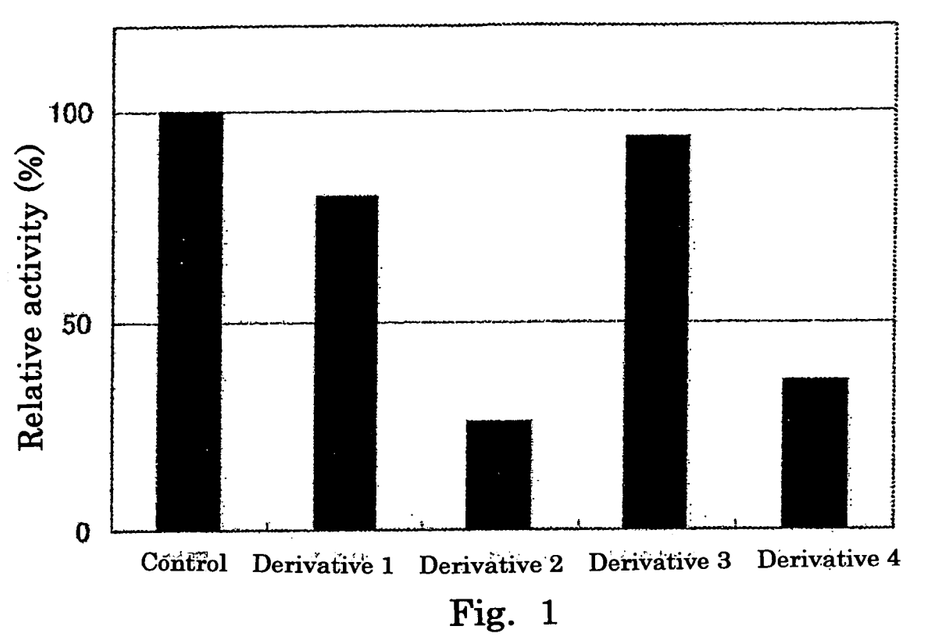
FIG. 1 is a graph showing an inhibitory effect of a hexuronic acid derivative on activity of HS6ST in the case that CDSNS heparin is used as a sulfate group acceptor substrate.

Inhibitory Effect of Hexuronic Acid Derivative on Activity of HS6ST to Transfer Sulfate Group to Completely Desulfated N-resulfated Heparin There was prepared 50 µl of a reaction solution containing 0.05 mol/l imidazole buffer (pH 6.8) comprising: 500 µmol/l of completely desulfated N-resulfated heparin (manufactured by Seikagaku Corporation, hereinafter also referred to as "CDSNS heparin") serving as a sulfate group acceptor substrate; 1 µmol/l of $^{35}$S-labeled 3'-phosphoadenosine-5'-phosphosulfate (enzymatically synthesized using adenosine triphosphate (ATP) and [$^{35}$S] sulfate according to the method described in Anal. Biochem., 148 (1985), pp. 303-310, hereinafter, 3'-phosphoadenosine-5'-phosphosulfate is also referred to as "PAPS"); 0.4 unit of HS6ST; 3.75 µg of protamine hydrochloride (manufactured by Sigma); 0.15 mol/l of NaCl; and 10 mmol/l of a hexuronic acid derivative (any one of Derivatives 1 to 4), and the reaction was performed by incubation at 37° C. for 20 minutes. An experimental group to which no hexuronic acid derivative was added was used as a control.

After the reaction, the reaction solution was separated by high-performance liquid chromatography (hereinafter also referred to as "HPLC") using Fast Desalting Column HR10/10 column (manufactured by Amersham Biosciences, KK) (analysis conditions: flow rate of 2.0 ml/minute, temperature: 20° C.), and the peak of CDSNS heparin was collected. Thereafter, the radioactivity in the fraction was quantified with a liquid scintillation counter to determine incorporation of radioactivity into CDSNS heparin (FIG. 1).

As a result, it was found that all Derivatives 1 to 4 exerted inhibitory effects on HS6ST, and in particular, Derivatives 2 and 4 each having a β-glycosidic bond exerted stronger inhibitory effects.

Example 2

Figure 2:
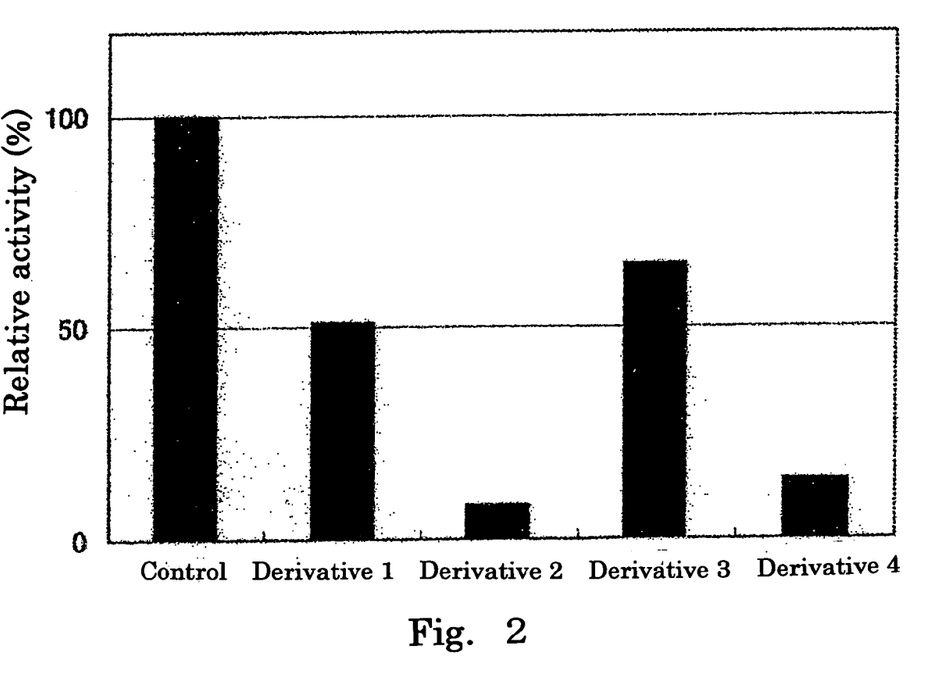
FIG. 2 is a graph showing an inhibitory effect of a hexuronic acid derivative on activity of HS2ST in the case that heparan sulfate is used as a sulfate group acceptor substrate.
Figure 3:
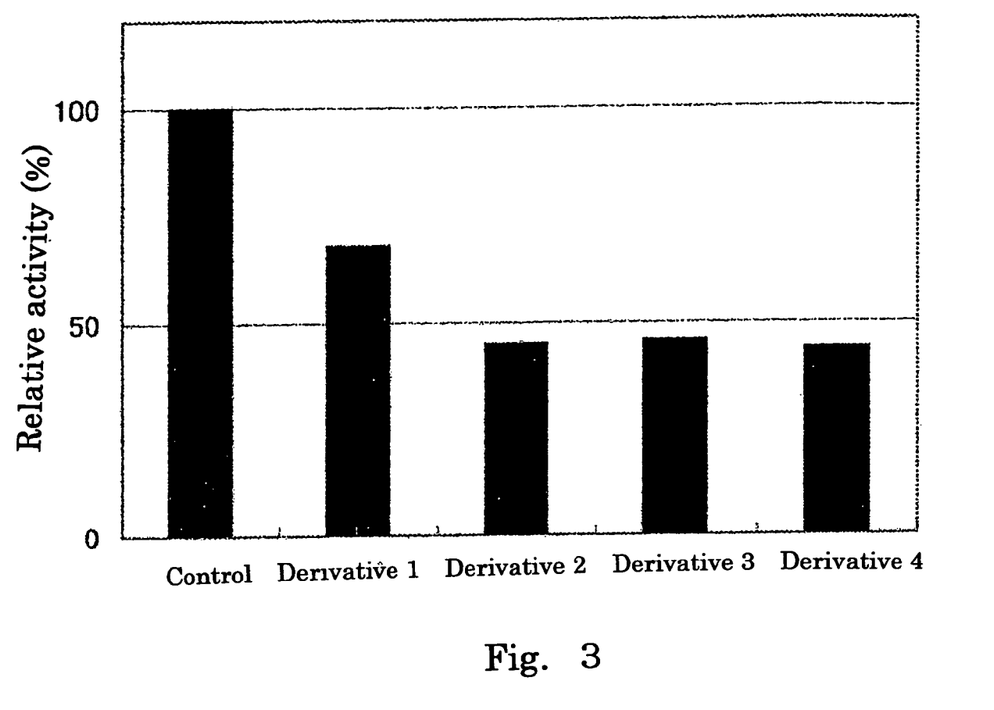
FIG. 3 is a graph showing an inhibitory effect of a hexuronic acid derivative on activity of HS6ST in the case that heparan sulfate is used as a sulfate group acceptor substrate.

Inhibitory Effect of Hexuronic Acid Derivative on Activity to Transfer a Sulfate Group to Heparan Sulfate by HS2ST and HS6ST, Respectively There was prepared 50 µl of a reaction solution containing 0.05 mol/l imidazole buffer (pH 6.8) comprising: 500 µmol/l of heparan sulfate (derived from swine aorta, manufactured by Seikagaku Corporation) serving as a sulfate group acceptor substrate; 1 µmol/l of $^{35}$S-labeled PAPS; 0.4 unit of HS2ST or HS6ST; 3.75 µg of protamine hydrochloride (manufactured by Sigma); 0.15 mol/l of NaCl; and 10 mmol/l of a hexuronic acid derivative (any one of Derivatives 1 to 4), and the reaction was performed by incubation at 37° C. for 20 minutes. An experimental group to which no hexuronic acid derivative was added was used as a control.

After the reaction, the reaction solution was separated by HPLC using Fast Desalting Column HR10/10 column (manufactured by Amersham Biosciences, KK) (analysis conditions: flow rate of 2.0 ml/minute, temperature: 20° C.), and the peak of heparan sulfate was collected. Thereafter, the radioactivity in the fraction was quantified with a liquid scintillation counter to determine incorporation of radioactivity into heparan sulfate (HS2ST: FIG. 2, HS6ST: FIG. 3).

As a result, it was found that all Derivatives 1 to 4 exerted inhibitory effects on HS2ST and HS6ST, and in particular, Derivatives 2 and 4 each having a β-glycosidic bond exerted stronger inhibitory effects on HS2ST.

Example 3

Inhibition Curves of Derivative 2 Against HS2ST and HS6ST, Respectively

Figure 4:
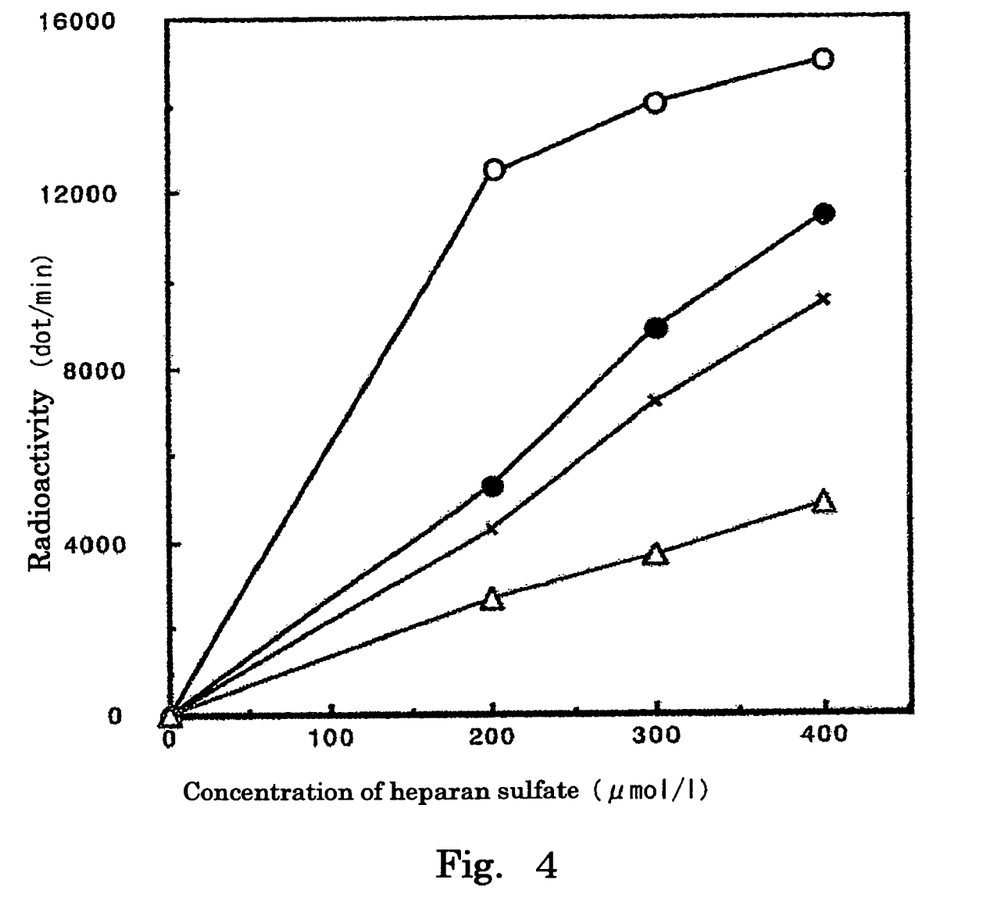
FIG. 4 is a graph showing an inhibition curve of Derivative 2 against HS2ST activity. The open circles represent the enzyme activity of HS2ST in the case that Derivative 2 was not added, the filled circles represent the enzyme activity of HS2ST in the case that Derivative 2 was added at a concentration of 1 mmol/l, the crosses represent the enzyme activity of HS2ST in the case that Derivative 2 was added at a concentration of 3 mmol/l, and the triangles represent the enzyme activity of HS2ST in the case that Derivative 2 was added at a concentration of 10 mmol/l.
Figure 5:
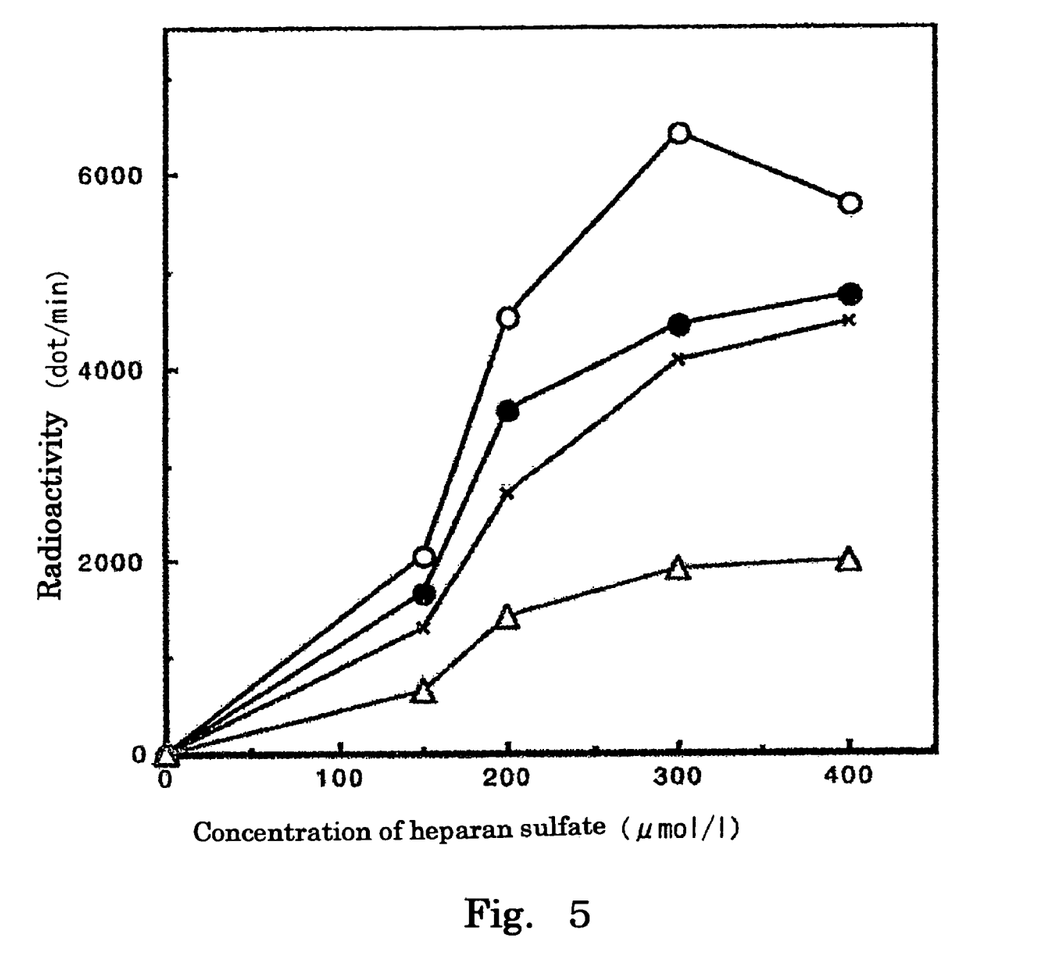
FIG. 5 is a graph showing an inhibition curve of Derivative 2 against HS6ST activity. The open circles represent the enzyme activity of HS6ST in the case that Derivative 2 was not added, the filled circles represent the enzyme activity of HS6ST in the case that Derivative 2 was added at a concentration of 1 mmol/l, the crosses represent the enzyme activity of HS6ST in the case that Derivative 2 was added at a concentration of 3 mmol/l, and the triangles represent the enzyme activity of HS6ST in the case that Derivative 2 was added at a concentration of 10 mmol/l.

Under the same conditions as described in Example 2, the concentration of heparan sulfate was changed from 0 to 400 µmol/l, while the concentration of Derivative 2 was changed from 0 to 10 mmol/l, and incorporation of radioactivity into heparan sulfate was determined to create inhibition curves of Derivative 2 (HS2ST: FIG. 4, HS6ST: FIG. 5).

As a result, it was found that Derivative 2 exerted an inhibitory effect on each of HS2ST and HS6ST in a concentration-dependent manner.

Example 4

Figure 6:
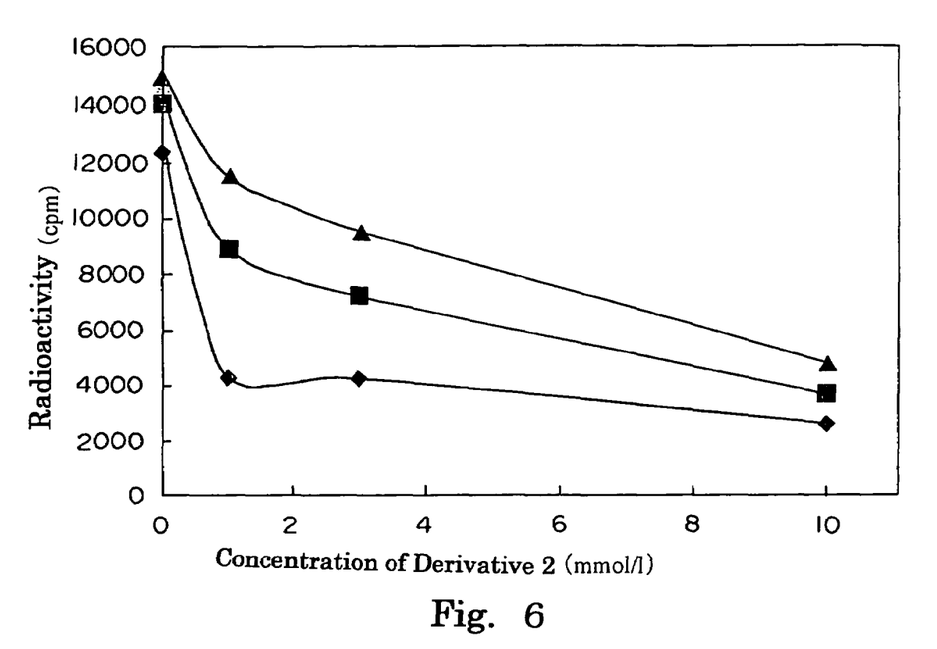
FIG. 6 is a graph showing effects of the concentrations of heparan sulfate and Derivative 2 on the HS2ST activity. The triangles represent the enzyme activity of HS2ST in the case that the concentration of heparan sulfate is 400 μmol/l, the squares represent the enzyme activity of HS2ST in the case that the concentration of heparan sulfate is 300 μmol/l, and the rhombuses represent the enzyme activity of HS2ST in the case that the concentration of heparan sulfate is 200 μmol/l.
Figure 7:
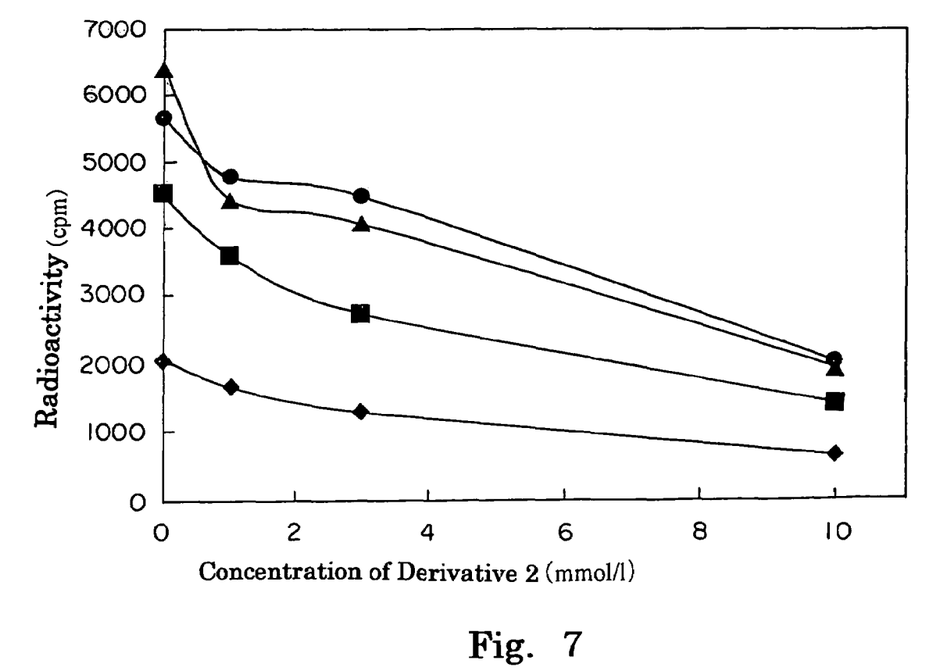
FIG. 7 is a graph showing effects of the concentrations of heparan sulfate and Derivative 2 on the HS6ST activity. The circles represent the enzyme activity of HS6ST in the case that the concentration of heparan sulfate is 400 μmol/l, the triangles represent the enzyme activity of HS6ST in the case that the concentration of heparan sulfate is 300 μmol/l, the squares represent the enzyme activity of HS6ST in the case that the concentration of heparan sulfate is 200 μmol/l, and the rhombuses represent the enzyme activity of HS6ST in the case that the concentration of heparan sulfate is 150 μmol/l.

Relationship Between Sulfate Group-transferring Activity of HS2ST and HS6ST Respectively, and Heparan Sulfate Concentration and Hexuronic Acid Derivative Concentration There was prepared 50 µl of a reaction solution containing 0.05 mol/l imidazole buffer (pH 6.8) comprising: 150 to 400 µmol/l of heparan sulfate (derived from swine aorta, manufactured by Seikagaku Corporation) serving as a sulfate group acceptor substrate; 1 µmol/l of $^{35}$S-labeled PAPS; 0.4 unit of HS2ST or HS6ST; 3.75 µg of protamine hydrochloride (manufactured by Sigma); 0.15 mol/l of NaCl; and 0 to 10 mmol/l of Derivative 2, and the reaction was performed by incubation at 37° C. for 20 minutes.

After the reaction, the reaction solution was separated by HPLC using Fast Desalting Column HR10/10 column (manufactured by Amersham Biosciences, KK) (analysis conditions: flow rate of 2.0 ml/minute, temperature: 20° C.), and the heparan sulfate peak was collected. Thereafter, the radioactivity in the fraction was quantified with a liquid scintillation counter to determine incorporation of radioactivity into heparan sulfate (HS2ST: FIG. 6, HS6ST: FIG. 7).

As a result, it was found that Derivative 2 exerted an inhibitory effect on each of HS2ST and HS6ST in a concentration-dependent manner.

Example 5

Effect of Derivative 2 on Heparan Sulfate Synthesis by Cultures Cells

Derivative 2 was added at a concentration of 10 mmol/l to each of culture media (Dulbecco's modified Eagle's medium containing 10 fetal bovine serum (DMEM-F12: pH 7.2)) of CHO k1 cells that mean k1 strains of the cultured cell derived from Chinese hamster ovary (CHO cell) (JCRB9018) and CHO-k(t) cells that mean k(t) strains prepared by stably transfecting a DNA coding for HS6ST to the k1 cell according to JP11-69983A, and subsequently the cells of each strains were cultured for 48 hours.

After the culture, glycosaminoglycan was collected from the cultured cells using a DEAE-Sepharose column, and according to the method described in Shin-Seikagaku Jikken Kouza 3, Sugars II, pp. 54-59, the collected glycosaminoglycan (1.0 mg) was dissolved in 220 µl of 20 mmol/l sodium acetate (pH 7.0) containing 2 mmol/l calcium acetate, and a glycosaminoglycan-degrading enzyme (20 mU of heparitinase, 20 mU of heparitinase I and II (all of which are manufactured by Seikagaku Corporation)) was added thereto, followed by reaction at 37° C. for 2 hours. After the reaction, 20 µl of the reaction solution was analyzed by HPLC. For HPLC, separation was performed according to reverse-phase ion-pair chromatography described in Biol. Chem., 275 (2000), pp. 2269-2275, and then fluorescent labeling was performed by the post-column method, followed by quantification. The analysis was performed at a flow rate of 1.1 ml/minute using Senshu PAK Docosil column (proprietary name: 4.6×150 mm) manufactured by Senshu Scientific Co., Ltd., and the detection was performed by determination of an absorbance at an emission wavelength of 410 nm caused by excitation at an excitation wavelength of 346 nm. Of unsaturated disaccharides generated by digestion with the glycosaminoglycan-degrading enzyme, the following compositions were calculated:

2-acetamide-2-deoxy-4-O-(4-deoxy-α-L-threo-hex-enopyranosyluronic acid)-D-glucose (hereinafter referred to as "ΔDi-OS"), 2-deoxy-2-sulfamino-4-O-(4-deoxy-α-L-threo-hex-4-enopyranosyluronic acid)-D-glucose (hereinafter referred to as "ΔDi-NS"), 2-acetamide-2-deoxy-4-O-(4-deoxy-α-L-threo-hex-4-enopyranosyluronic acid)-6-O-sulfo-D-glucose (hereinafter referred to as "Di-6S"), 2-deoxy-2-sulfamino-4-O-(4-deoxy-α-L-threo-hex-4-enopyranosyluronic acid)-6-O-sulfo-D-glucose (hereinafter referred to as "Di-(N,6)diS"), 2-acetamide-2-deoxy-4-O-(4-deoxy-2-O-sulfo-α-L-threo-hex-4-enopyranosyluronic acid)-6-O-sulfo-D-glucose (hereinafter referred to as "ΔDi-(U,6)diS"), and 2-deoxy-2-sulfamino-4-O-(4-deoxy-2-O-sulfo-α-L-threo-hex-4-enopyranosyluronic acid)-6-O-sulfo-D-glucose (hereinafter referred to as "ADi-(N,6,U)triS")

(Table 1: In the table, "CHO-k(t)/C" and "CHOk1/C" represent control groups in each of which Derivative 2 was not added).

TABLE 1

|  | Δ Di-OS | Δ Di-NS | Δ Di-6S | Δ Di-(N, 6)diS | Δ Di-(U, 6)diS | Δ Di-(N, 6, U)triS | 6S amount |
|---|---|---|---|---|---|---|---|
| CHO-k (t) | 56.3% | 19.4% | 2.7% | 2.9% | 9.5% | 9.1% | 14.7% |
| CHO-k (t)/C | 46.9% | 19.1% | 6.4% | 5.0% | 7.1% | 15.6% | 27.0% |
| CHOk1 | 58.3% | 20.8% | 0.8% | 0.5% | 12.6% | 7.0% | 8.3% |
| CHOk1/C | 50.9% | 19.5% | 2.5% | 1.2% | 11.6% | 14.4% | 18.1% |

As a result, it was found that, in both CHO-k(t) group and CHOk1 group, the amount of unsaturated disaccharides having sulfate groups at 6-position decreased significantly compared with the control. The results show that the effect of HS6ST to transfer a sulfate group to the 6-position of a glucosamine residue of heparan sulfate was inhibited.

INDUSTRIAL APPLICABILITY

The present invention provides a novel heparin/heparan sulfate sulfotransferase inhibitor using a hexuronic acid derivative.

What is claimed is:

1. A method of inhibiting a heparin/heparan sulfate sulfotransferase by contacting the heparin/heparan sulfate sulfotransferase with a hexuronic acid derivative represented by the following formula 1 or a salt thereof, wherein the heparin/heparan sulfate sulfotransferase has activity to transfer a sulfate group to a hydroxyl group at 6-position of a glucosamine residue or to a hydroxyl group at 2-position of a hexuronic acid residue in a heparin skeleton, (1)

wherein each of $R_1$, $R_2$, and $R_3$ independently represent(s) $SO_3^-$ or H, provided that at least one thereof represents $SO_3^-$; X represents $OR_4$, $R_4$ independently represents H, alkyl which may have a substituent selected from alkoxy group and acyloxy group, alkenyl, alkynyl, acyl, aryl, or aralkyl group; one of $R_5$ and $R_6$ represents COOH while the other represents H; and the wavy line represents α-glycosidic bond or β-glycosidic bond, wherein said acyl group is represented as —CO—$R_7$ in which $R_7$ represents a group selected from alkyl which may have a substituent selected from alkoxy group and acyloxy group, alkenyl, alkynyl, aryl, and aralkyl groups.

2. The method according to claim 1, wherein said $R_4$ independently represents alkyl group having 1 to 20 carbon atoms which may have a substituent selected from alkoxy group and acyloxy group.

3. The method according to claim 1, wherein said $R_4$ independently represents alkyl group having 1 to 6 carbon atoms which may have a substituent selected from alkoxy group and acyloxy group.

4. The method according to claim 1, wherein said $R_4$ independently represents alkyl group having 1 to 4 carbon atoms which may have a substituent selected from alkoxy group and acyloxy group.

* * * * *

UNITED STATES PATENT AND TRADEMARK OFFICE
CERTIFICATE OF CORRECTION

| | |
|---|---|
| PATENT NO. | : 7,396,818 B2 |
| APPLICATION NO. | : 10/557652 |
| DATED | : July 8, 2008 |
| INVENTOR(S) | : Kimata et al. |

It is certified that error appears in the above-identified patent and that said Letters Patent is hereby corrected as shown below:

First Page, Column 1, Other Publications, Line 5, "GIcNAc *N*-Deacetylasel," should be changed to --GlcNAc *N*-Deacetylase/*N*-Sulfotransferase Family,"--

First Page, Column 2, Other Publications, Line 14, "*N*-Deacetylase/*N*-" should be changed to --*N*-Deacetylase/*N*- --

Column 1, Line 55, "NDST4) each having" should be changed to --NDST-4) each having--

Column 2, Line 65, "and $R_4$ represents H." should be changed to --and $R_6$ represents H.--

Column 5, Line 15, "the other is H" should be changed to --the other is H,--

Column 5, Line 18, "$R_4$ (($R_4$), $(R_4)_3$) binds to" should be changed to --$R_4$ (($R_4$)$_2$, $(R_4)_3$) binds to--

Column 6, Line 44, "OXO, carboxyl (COOH)," should be changed to --oxo, carboxyl (COOH),--

Column 9, Line 46, "in Anal. Biocham.," should be changed to --in Anal. Biochem.,--

Column 12, Line 3, "to as "ADi-N,6,U)triS")" should be changed to --to as "ΔDi-N,6,U)triS")--

UNITED STATES PATENT AND TRADEMARK OFFICE
CERTIFICATE OF CORRECTION

PATENT NO. : 7,396,818 B2
APPLICATION NO. : 10/557652
DATED : July 8, 2008
INVENTOR(S) : Kimata et al.

It is certified that error appears in the above-identified patent and that said Letters Patent is hereby corrected as shown below:

Column 12, Line 57, "wherein each of" should be changed to --wherein, each of--

Signed and Sealed this

Twenty-fourth Day of March, 2009

JOHN DOLL
*Acting Director of the United States Patent and Trademark Office*